(12) United States Patent
Johnson et al.

(10) Patent No.: US 9,192,427 B2
(45) Date of Patent: Nov. 24, 2015

(54) BIPOLAR CUTTING END EFFECTOR

(75) Inventors: Kristin D. Johnson, Louisville, CO (US); Gary M. Couture, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1593 days.

(21) Appl. No.: 12/399,614

(22) Filed: Mar. 6, 2009

(65) Prior Publication Data
US 2009/0234354 A1    Sep. 17, 2009

Related U.S. Application Data

(60) Provisional application No. 61/035,452, filed on Mar. 11, 2008.

(51) Int. Cl.
| A61B 18/18 | (2006.01) |
| A61B 18/04 | (2006.01) |
| A61B 18/14 | (2006.01) |
| A61B 18/00 | (2006.01) |

(52) U.S. Cl.
CPC ... *A61B 18/1402* (2013.01); *A61B 2018/00601* (2013.01); *A61B 2018/1412* (2013.01)

(58) Field of Classification Search
CPC ............. A61B 18/00; A61B 2018/00059; A61B 2018/00607; A61B 2018/00601; A61B 18/04; A61B 18/08; A61B 18/082; A61B 18/085; A61B 18/12; A61B 18/14; A61B 2018/1405; A61B 2018/1475; A61B 2018/1412; A61B 18/1402
USPC ..................... 606/32, 41, 45, 48, 50
See application file for complete search history.

(56) References Cited

U.S. PATENT DOCUMENTS

| 4,043,342 | A |   | 8/1977  | Morrison, Jr. |
| 4,483,338 | A | * | 11/1984 | Bloom et al. .................. 606/50 |
| 4,674,499 | A | * | 6/1987  | Pao ..................... A61B 18/1402 604/20 |
| 4,706,667 | A | * | 11/1987 | Roos ............................ 606/48 |
| 4,805,616 | A |   | 2/1989  | Pao |
| 5,085,659 | A |   | 2/1992  | Rydell |

(Continued)

FOREIGN PATENT DOCUMENTS

| CA | 2104423 | 2/1994 |
| DE | 2415263 | 10/1975 |

(Continued)

OTHER PUBLICATIONS

European Search Report based on European Application No. EP 09 15 4850 dated Jul. 20, 2009.

(Continued)

*Primary Examiner* — Kami A Bosworth
*Assistant Examiner* — Bradley G Thomas, Jr.

(57) ABSTRACT

An electrosurgical instrument for cutting tissue includes a blade assembly. The blade assembly includes a first electrode having a first pre-selected shape and a first distal edge, and a second electrode disposed in spaced relation relative to the first electrode. The second electrode includes a second pre-selected shape and a second distal edge, where the first distal edge and the second distal edge form an electrically conductive tissue cutting surface extending along the distal end of the instrument. The tissue cutting surface is adapted to connect to a source of electrosurgical energy such that the tissue cutting surface is capable of conducting electrosurgical energy through tissue adjacent thereto to effectively cut tissue.

19 Claims, 4 Drawing Sheets

(56) References Cited

U.S. PATENT DOCUMENTS

| | | | |
|---|---|---|---|
| 5,395,360 | A | 3/1995 | Manoukian |
| 5,702,369 | A | 12/1997 | Mercereau |
| 5,810,764 | A | 9/1998 | Eggers et al. |
| 6,283,961 | B1 | 9/2001 | Underwood et al. |
| 6,358,249 | B1 | 3/2002 | Chen et al. |
| 6,558,385 | B1 | 5/2003 | McClurken et al. |
| 6,616,661 | B2 | 9/2003 | Wellman et al. |
| 6,942,662 | B2 | 9/2005 | Goble et al. |
| 7,070,597 | B2 | 7/2006 | Truckai et al. |
| 7,179,255 | B2 | 2/2007 | Lettice et al. |
| 7,270,664 | B2 | 9/2007 | Johnson et al. |
| 7,318,823 | B2 | 1/2008 | Sharps et al. |
| 2002/0049442 | A1 | 4/2002 | Roberts et al. |
| 2004/0030330 | A1 | 2/2004 | Brassell et al. |
| 2008/0045947 | A1 | 2/2008 | Johnson et al. |
| 2008/0195093 | A1 | 8/2008 | Couture et al. |
| 2009/0088745 | A1 | 4/2009 | Hushka et al. |
| 2009/0182327 | A1 | 7/2009 | Unger |
| 2009/0187188 | A1 | 7/2009 | Guerra et al. |

FOREIGN PATENT DOCUMENTS

| | | | |
|---|---|---|---|
| DE | 2514501 | | 10/1976 |
| DE | 2627679 | | 1/1977 |
| DE | 34 23 356 | | 1/1986 |
| DE | 3612646 | | 4/1987 |
| DE | 8712328 | | 3/1988 |
| DE | 4303882 | | 8/1994 |
| DE | 4403252 | | 8/1995 |
| DE | 19515914 | | 7/1996 |
| DE | 29616210 | | 1/1997 |
| DE | 19608716 | | 4/1997 |
| DE | 19751106 | | 5/1998 |
| DE | 19751108 | | 5/1999 |
| DE | 19738457 | | 1/2009 |
| EP | 0 509 670 | | 10/1992 |
| EP | 0509670 | A | 10/1992 |
| EP | 0 923 907 | | 6/1999 |
| EP | 0 950 378 | | 10/1999 |
| EP | 1 025 807 | | 8/2000 |
| EP | 1159926 | | 12/2001 |
| GB | 623316 | | 5/1949 |
| GB | 1490585 | | 11/1977 |
| GB | 2214430 | A | 6/1989 |
| GB | 2213416 | A | 8/1989 |
| GB | WO97/00647 | * | 1/1997 |
| JP | 61-501068 | | 9/1984 |
| JP | 65-502328 | | 3/1992 |
| JP | 5-5106 | | 1/1993 |
| JP | 5-40112 | | 2/1993 |
| JP | 06343644 | | 12/1994 |
| JP | 07265328 | | 10/1995 |
| JP | 08056955 | | 3/1996 |
| JP | 08252263 | | 10/1996 |
| JP | 09010223 | | 1/1997 |
| JP | 11244298 | | 9/1999 |
| JP | 2000-342599 | | 12/2000 |
| JP | 2000-350732 | | 12/2000 |
| JP | 2001-008944 | | 1/2001 |
| JP | 2001-029356 | | 2/2001 |
| JP | 2001-128900 | | 5/2001 |
| SU | 401367 | | 11/1974 |
| WO | WO 93/19681 | | 10/1993 |
| WO | WO 95/20360 | * | 8/1995 |
| WO | WO95/20360 | * | 8/1995 |
| WO | WO 97/00647 | * | 1/1997 |
| WO | WO 97/18768 | * | 5/1997 |
| WO | WO 97/24993 | | 7/1997 |

OTHER PUBLICATIONS

U.S. Appl. No. 12/336,970, filed Dec. 17, 2008.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/255,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.

(56) References Cited

OTHER PUBLICATIONS

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" . Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2. dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.

(56) References Cited

OTHER PUBLICATIONS

Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
European Exam Report dated Oct. 30, 2012 from corresponding European Application No. 09 154 850.3.

* cited by examiner

BIPOLAR CUTTING END EFFECTOR

CROSS-REFERENCE TO RELATED APPLICATIONS

This application claims the benefit of priority to U.S. Provisional Application Ser. No. 61/035,452 entitled "BIPOLAR CUTTING END EFFECTOR" filed Mar. 11, 2008 by Kristin D. Johnson, which is incorporated by reference herein.

BACKGROUND

1. Technical Field

The present disclosure relates to an electrode assembly that allows a user to cut tissue. More particularly, the present disclosure relates to a blade assembly having a unique electrode configuration assembled with geometrical variations that vary current densities and electrical fields.

2. Background of Related Art

Many surgical procedures are enhanced by the use of an electrosurgical instrument for cutting, spot coagulation, point coagulation, and sealing of tissue during an operation. For example, thermal energy may be used in general surgery as a substitute for a scalpel to assist in the control of blood flow. Procedures where electrosurgical devices are used include open and laparoscopic/minimally invasive general surgery as well as specialty areas, such as arthroscopic surgery, orthopedic surgery, cardiovascular surgery, cosmetic/reconstructive surgery, neurosurgery, and urologic surgery. Application generally includes manually contacting the electrosurgical instrument directly to the appropriate area of tissue.

Various surgical instruments are known for treating tissue. For example, surgical instruments used for tissue division, dissection, ablation, or for arresting blood loss and coagulation are well-known. In a particular application, for example, a coagulation instrument has an electrode used in conjunction with a heated probe to arrest bleeding. However, since the probe must come into close contact with the tissue, the probe may adhere to the tissue during probe removal and possibly cause repeat bleeding.

As can be appreciated, the overall success of creating an effective cut with cutting instruments is greatly reliant upon the user's expertise, vision, dexterity, and experience in judging the appropriate force, and length of reciprocation of a knife or electrosurgical cutting device to uniformly, consistently and effectively cut tissue along an ideal cutting plane. Thermal spread, charring, aberrant current densities and electrical fields may reduce the overall success rate of a cut by diminishing the surgeon's ability. Known electrosurgical cutting instruments are problematic for they do not attempt to reduce and/or limit undesirable visual effects such as thermal spread, charring, or take into account aberrant current densities and/or electrical fields which may decrease the accuracy of the cutting device. Moreover, energy-based medical devices often are limited by the placement and geometries of the electrodes on the device, an integral element of their use. As electrosurgical instruments are often manually applied to the tissue during the surgery to effect a cut, precise control by the surgeon, taking into account the placement and geometries of the electrodes on the device, is required. In known devices, placement and geometries of the electrodes are problematic in that they may increase the length of the procedure (particularly when cutting a significant number of vessels) and/or may contribute to imprecise separation of the tissue along the cutting line due to the misalignment or misplacement of the severing instrument along the center of the tissue cut.

Some prior art devices include an electrosurgical instrument having a nonconductive handle that holds a blade assembly. The blade assembly includes a plurality of electrodes and an insulation member separating the electrodes. An active center electrode of specified thickness with a recessed tip is mounted to an extruded insulation member so that it extends outwardly from the insulation member to form a cutting edge. However, such a device limits the surgeon's ability to visually and manually regulate the placement and amount of force of the blade assembly to the tissue. Moreover, such a device does not attempt to vary a tissue cut by providing an electrode configuration that modifies current densities and electrical fields around the device.

New electrosurgical blades having different placement and geometries of the electrodes are continuously sought after to satisfy different surgeons, as well as alter aberrant current densities and/or electrical field formation around the device.

SUMMARY

The present disclosure relates to an electrosurgical instrument which generally includes a blade assembly. The blade assembly includes a first electrode having a first pre-selected shape including a first distal edge, a second electrode disposed in spaced relation relative to the first electrode, the second electrode having a second pre-selected shape and a second distal edge. The first distal edge and the second distal edge form an electrically conductive tissue cutting surface extending along the distal end of the electrosurgical instrument. The tissue cutting surface may be adapted to connect to a source of electrosurgical energy such that the tissue cutting surface is capable of conducting electrosurgical energy through tissue adjacent thereto to effectively cut tissue.

The electrosurgical instrument may further include an insulator configured to support each electrode. In embodiments, the first electrode may have a first length, and the second electrode which may have a second length. The first length may be longer than the second length. Optionally, the first length may be shorter than the second length. The first electrode and second electrode may be concentric. Also, the first and second electrodes may be substantially tube shaped. The first and second electrodes may be substantially square shaped. In embodiments, the first and second electrodes may have a gap therebetween. In embodiments, the first and second electrodes are disposed in an angular relationship relative to one another. The first electrode may be an active electrode, or optionally, the second electrode may be an active electrode.

In embodiments, the insulative handle may further include a distal cover configured to cover over the electrically conductive tissue cutting surface. The cover may be connected to a handle of an electrosurgical instrument by a hinge.

There is also disclosed an electrosurgical instrument which generally includes an insulative housing, and a blade assembly having concentric first and second electrodes each having a different polarity and configured such that electrosurgical energy flows from the first electrode to the second electrode. The first and second electrodes may be disposed in spaced relation relative to one another. The blade assembly may also include an electrically conductive tissue cutting surface extending along the distal end thereof. The tissue cutting surface may be adapted to connect to a source of electrosurgical energy such that the tissue cutting surface is capable of conducting electrosurgical energy through tissue contacted therewith to effectively cut tissue. The instrument may further include an insulator configured to support each electrode.

The insulative housing may include a distal cover configured to cover the electrically conductive tissue cutting surface. In some embodiments, the insulator is configured to at least partially extend to a position which is at least substantially flush with the electrically conductive tissue cutting surface.

BRIEF DESCRIPTION OF THE DRAWINGS

Various embodiments of the presently disclosed tissue cutting device are disclosed herein with reference to the drawings, wherein.

DETAILED DESCRIPTION

Figure 1:
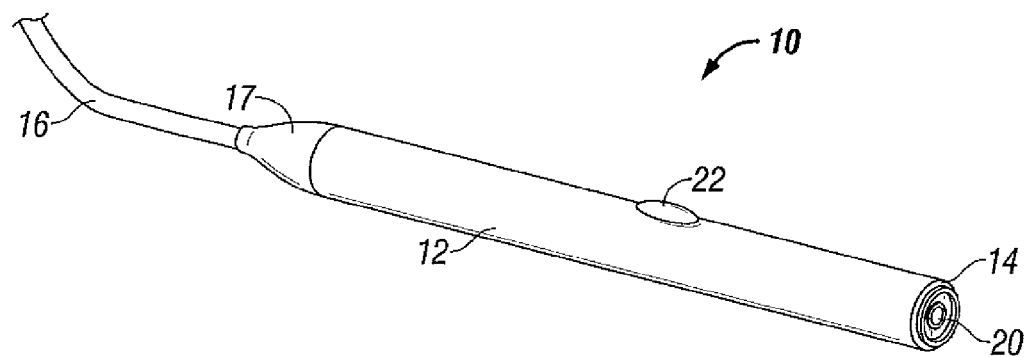
FIG. 1 is a perspective view of one embodiment of the electrosurgical instrument.

Embodiments of the presently disclosed electrosurgical instrument will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

For the purposes herein, tissue/vessel cutting or tissue/vessel division is believed to occur when heating of the tissue/vessel leads to expansion of intracellular and/or extra-cellular fluid, which may be accompanied by cellular vaporization, desiccation, fragmentation, collapse and/or shrinkage along a so-called "cut zone" in the tissue/vessel. By focusing the electrosurgical energy and heating in the cut zone, the cellular reactions are localized creating a fissure. Localization is achieved by regulating the tissue/vessel condition and energy delivery, which may be controlled by utilizing one or more of the various geometrical electrode and insulator configurations described herein. The cut process may also be controlled by utilizing a suitable generator and feedback algorithm (and one or more of the hereindescribed geometrical configurations of the electrode and insulator assemblies), which increases the localization and maximizes the so-called "cutting effect".

Various known factors, such as those described in U.S. patent application Ser. No. 11/418,876, entitled VESSEL SEALING INSTRUMENT WITH ELECTRICAL CUTTING MECHANISM filed on May 5, 2006 may contribute and/or enhance tissue/vessel division using electrosurgical energy. For example, localizing or focusing electrosurgical energy in the cut zone during the cutting process while minimizing energy effects to surrounding tissues enhances tissue/vessel division using electrosurgical energy. Factors that enhance or contribute to tissue/vessel division may be employed individually or in any combination to achieve a desired cutting effect. For the purposes herein the term "cut effect" or "cutting effect" refers to the actual division of tissue by one or more of the electrical or electromechanical methods or mechanisms described below. The term "cutting zone" or "cut zone" refers to the region of tissue/vessel where cutting will take place. The term "cutting process" refers to steps that are implemented before, during and/or after tissue/vessel division that tend to influence the tissue/vessel as part of achieving the cut effect.

For the purposes herein the terms "tissue" and "vessel" may be used interchangeably since it is believed that the present disclosure may be employed to cut and seal tissue or cut and seal vessels utilizing the same inventive principles described herein.

Many of the blade assemblies described herein employ one or more of the factors for enhancing tissue division, such as localizing or focusing electrosurgical energy in the cut zone during the cutting process while minimizing energy effects to surrounding tissues. Further, many of the electrode assemblies described herein utilize various geometrical configurations of electrodes, cutting elements, insulators, partially conductive materials, semiconductors, and combinations thereof to produce or enhance the cutting effect. In addition, by controlling or regulating the electrosurgical energy from the generator in any of the ways described above, tissue cutting may be initiated, enhanced or facilitated within the tissue cutting zone. For example, the geometrical configuration of the electrodes and insulators may be configured to produce a so-called "cut effect", which may be directly related to the amount of vaporization or fragmentation at a point in the tissue or the power density, temperature density and/or mechanical stress applied to a point in the tissue. The geometry of the electrodes may be configured such that the surface area ratios between the electrical poles focus electrical energy at the tissue. Moreover, the geometrical configurations of the electrodes and insulators may be designed such that they act like electrical (or thermal) sinks or insulators to influence the heat effect within and around the tissue during the sealing or cutting processes.

Referring now to FIG. 1, an electrosurgical device 10 for use in connection with surgical procedures is shown. For the purposes herein, either an endoscopic instrument, such as one suitable for an IMA takedown procedure, catheter-type application, and/or other instrument suitable for use in electrosurgery may be utilized with the electrosurgical blade assembly described herein. Different electrical and mechanical connections and considerations may apply to each particular type of instrument; however, the novel aspects with respect to the electrode assembly and its operating characteristics remain generally consistent with respect to various designs.

Electrosurgical instrument 10 includes a housing or insulative handle 12 that has a slim design so that it fits comfortably into the hand of a surgeon or can be adapted for use in a catheter-type application, and/or other instrument suitable for use in electrosurgery. A bipolar blade assembly 20 that includes the electrode assembly (not explicitly shown) is disposed upon the distal end 14 of handle 12. Handle 12 also includes at least one cable or wire 16 that is secured to the proximal end 17 of handle 12 to facilitate the electrical connection of the bipolar blade assembly 20 and the electrosurgical generator 18.

Figure 2:
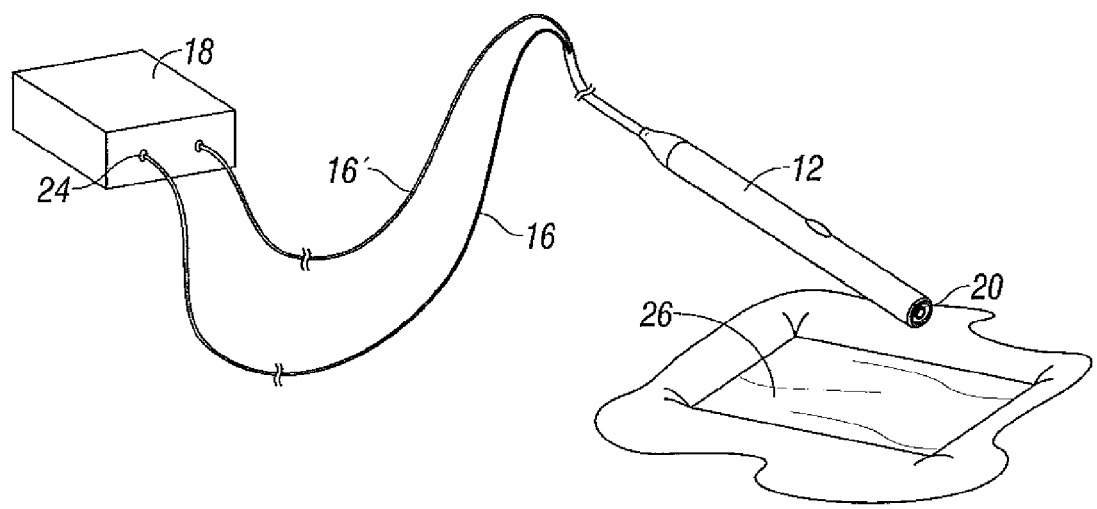
FIG. 2 is a schematic view of the instrument shown in FIG. 1 connected with an electrical wave form generator.

Referring now to FIG. 2, in some embodiments, two or more flexible insulated wires 16, 16' are provided sufficient in length to allow the surgeon unrestricted movement to contact tissue 26 while providing an effective electrical connection between the blade assembly 20 and the electrosurgical generator 18. Non-limiting examples of suitable electrosurgical generators 18 include the Surgistat™ Electrosurgical Generator, Valleylab Force FXT™ Electrosurgical Generator, and the Triad Energy Platform, all available from Valleylab—a division of Tyco HealthCare, and/or any other electrosurgical generator suitable for providing bipolar electrosurgical energy.

Referring back to FIG. 1, handle 12 may include a selector switch 22 such as a two-way; off/cut selector switch 22. The two-way selector switch allows the operator to select the desired mode of wave form emanating from the electrosurgical generator 18. Accordingly, the instrument can be used for cutting, coagulating, and combinations thereof. Referring again to FIG. 2, the active electrode (not explicitly shown) is connected to an active isolated output 24 of the electrosurgical generator 18 through its associated contact.

Figure 3A:
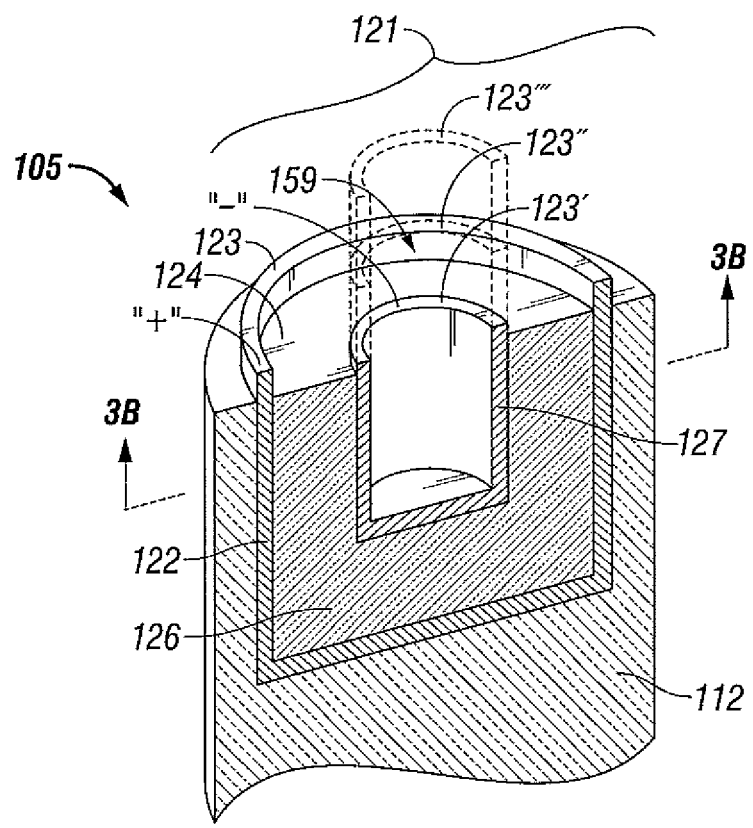
FIG. 3A is an enlarged, isometric view showing a cross-section of a blade assembly according to an embodiment of the present disclosure with electrical potentials identified for electrical cutting.

The general characteristics of the blade assembly will initially be described with respect to FIG. 3A while the changes to the other envisioned embodiments disclosed herein will become apparent during the description of each individual embodiment. Moreover, all of the following figures show the various electrical configurations and polarities during the cutting phase only. In embodiments suitable for the coagulation phase, the second electrode 127 is not necessarily energized such that the majority of the current is concentrated between the width of the first electrode 122.

Referring to FIG. 3A, a first geometrical configuration of a blade assembly 105 according to an embodiment of the present disclosure is shown having a first active electrode 122 and second electrode 127. First and second electrodes 122, 127, respectively, may have a non-stick coating on their respective electrode surface, or portion thereof. First electrode 122 includes a distal edge 123 and an inner space 124. Disposed within inner space 124 is second electrode 127 separated from the first electrode 122 by an insulator 126, which may be recessed between the first electrode 122 and second electrode 127 and/or form notches or set back areas 159. The second electrode 127 is configured with a smaller radius than the active electrode 122 such that during the cutting phase, electrosurgical energy is intensified to create a sufficient power density to effectively cut tissue proximate the second electrode 127.

Still referring to FIG. 3A, first electrode 122 has a first pre-selected shape including a first distal edge 123, and second electrode 127 is disposed in spaced relation relative to the first electrode 122. The second electrode 127 has a second pre-selected shape and a second distal edge 123'. The first distal edge 123 and the second distal edge 123' form the whole or part of an electrically conductive tissue cutting surface 121. Referring back to FIG. 1, when the blade assembly is placed on the distal end 14 of electrosurgical instrument 10, the electrically conductive tissue cutting surface 121 (not explicitly shown) extends along the distal end 14 of the instrument 10.

The electrically conductive tissue cutting surface 121 is adapted to connect to a source of electrosurgical energy such that the tissue cutting surface 121 is capable of conducting electrosurgical energy through tissue adjacent thereto to effect a cut of such tissue. In some embodiments, and as shown in the various figure drawings described hereafter, the blade assembly 105 may include a combination of both cutting and coagulating electrodes, and the electrically conductive tissue cutting surface 121.

The various electrical connections of the blade assembly 105 are configured to provide electrical continuity to the first electrode 122 and second electrode 127 including distal edges 123, and 123' of blade assembly 105. For example, cable leads (not explicitly shown) may be configured to include two or more different leads, namely, leads which carry different electrical potentials. The cable leads may be fed through housing 12 to connect to various electrical connectors (not explicitly shown) disposed within the proximal end of the handle 12, which ultimately connect to the electrically conductive surfaces 121 made of first electrode 122 and second electrode 127. As can be appreciated, the electrical connections may be permanently soldered to a shaft during the assembly process of a disposable instrument or, alternatively, selectively removable for use with a reposable instrument. Further, the various electrical connections from leads are typically dielectrically insulated from one another to allow selective and independent activation of either first electrode 122 and/or second electrode 127. The leads (and/or conductive pathways) do not encumber the movement of the electrosurgical device during the cutting of tissue.

Referring again to FIG. 3A, an electrical configuration of the blade assembly 105 is shown designed to effectively cut tissue disposed adjacent thereto. In some embodiments, second electrode 127 may serve as a cutting element that may be negatively charged. More particularly, and with respect to FIG. 3A, the blade assembly 105 includes distal edges 123 and 123' that may be used as conductive tissue contacting surfaces disposed along the distal end of the electrosurgical device 10 (e.g., extending substantially from the top to bottom of blade assembly 20 at distal end 14 in FIG. 1). First electrode 122 and second electrode 127 may be attached to the blade assembly 105 by stamping, by overmolding, by casting, by overmolding a casting, by coating a casting, by overmolding a stamped electrically conductive plate and/or by overmolding a metal injection molded plate or in other suitable ways. All of these manufacturing techniques may be employed to blade assembly 105 having an electrically conductive tissue contacting surface 121 disposed thereon for contacting and cutting tissue.

Still referring to FIG. 3A, blade assembly 105 includes an insulator or insulative material 126 disposed between the first electrode 122 and the second electrode 127. Non-limiting examples of materials used to make insulator 126 include ceramic material due to its hardness and inherent ability to withstand high temperature fluctuations. Alternatively, other non-limiting materials from which insulator 126 may be made include materials having a high Comparative Tracking Index (CTI) having a value in the range of about 300 to about 600 volts. Non-limiting examples of high CTI materials include nylons and syndiotactic polystyrenes. Other non-limiting suitable materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

Blade assembly 105 may include second electrode 127 which is suitable for use as a conductive cuffing element disposed substantially within or disposed on the insulator 126. In embodiments, the second electrode 127 may be configured to electrically energize tissue, such as previously formed sealed tissue, to cut the tissue. With respect to FIG. 3A, the electrode 127 is electrically conductive; however, may be made from an insulative material with a conductive coating disposed thereon or may be non-conductive.

The second electrode 127 may be configured to extend from insulator 123, and extend beyond the first electrode 122 such that the second electrode 127 may act as one or more stop members (i.e., creates a gap distance "G" between the distal end 123 of first electrode 122 and the tissue), which may promote accurate, consistent and effective tissue cutting. Accordingly, the distally extending length of the second electrode 127 may be longer than the distally extending length of the first electrode 122. As best shown in FIG. 3A, edge 123''' may be positioned distal to edge 123. Alternatively, second electrode 127 may be shorter than the first electrode 122 so that distal edge 123' is proximal to distal edge 123. However, the length of second electrode 127 may also be flush such that distal edge 123 and 123'' share a common plane.

With respect to FIG. 3A, the second electrode 127 may be substantially dull so as to not to prematurely cut the tissue prior to the electrosurgical activation. Thus, the surgeon is free to manipulate, contact, and push the tissue for cutting purposes without the second electrode 127 mechanically cutting into the tissue. Moreover, in this instance, tissue cutting can be achieved through either: 1) a combination of pushing the blade into the tissue and applying electrosurgical energy from the second electrode 127 through the tissue (e.g., the distal edge 123 as shown in FIG. 3A); or 2) applying electrosurgical energy from the second electrode 127 through the tissue and to the return edge 123.

The geometrical configuration of the first electrode 122 and second electrode 127 may play an important role in determining the overall effectiveness of the tissue cut. For example, the power density and/or current concentration around the second electrode 127 may be based upon the particular geometrical configuration of the second electrode 127 and/or the proximity to any return electrodes, e.g., edge 123. Certain geometries of the second electrode 127 may create higher areas of power density than other geometries. Moreover, the spacing of the first electrode 122 to these current concentrations affects the electrical fields through the tissue. Therefore, by configuring the second electrode 127 and edge 123 within close proximity to one another, the electrical power density remains high, which is important for cutting and the instrument will not short. The relative size of the second electrode 127 and/or the size of the edge 123 may be selectively altered depending upon a particular or desired purpose to produce a particular surgical effect.

Referring to FIG. 3A, blade assembly 105 shows non-limiting examples of the various polarities during the tissue cuffing phase. Further, the blade assembly 105 includes first electrode 122 disposed around the perimeter of second electrode 127. Insulator 126 electrically isolates first electrode 122 and second electrode 127 from one another allowing selective independent activation of the distal edges 123 and 123'.

Still referring to FIG. 3A, insulator 126 is set back a predetermined distance below distal edge 123 to define a recess 159 which, in some embodiments, may affect the overall power densities between the electrically activated surfaces during both the cutting and coagulating phases. Second electrode 127 may be disposed within and/or deposited on insulator 126 and extends outwardly therefrom to extend beyond the distal edge 123 by a predetermined distance.

During the cutting phase, the second electrode 127 is energized with a first electrical potential "−" and the first electrode is configured to a second electrical potential "+". This creates a concentrated electrical path between the potentials "−" and "+" through the tissue to cut the tissue adjacent a tissue seal.

As best seen in FIG. 3A, various electrical configurations of the blade assembly 105 are shown that are designed to effectively cut and/or seal tissue disposed adjacent thereto and the second electrode 127 which may serve as a cutting element. More particularly, and with respect to FIG. 3A, blade assembly 105 has first electrode 122 and second electrode 127, respectively, disposed in concentric relation to one another. Accordingly, the electrodes share a common center along axis A-A'. Axis A-A' may also be the longitudinal axis for the medical device.

Figure 3B:
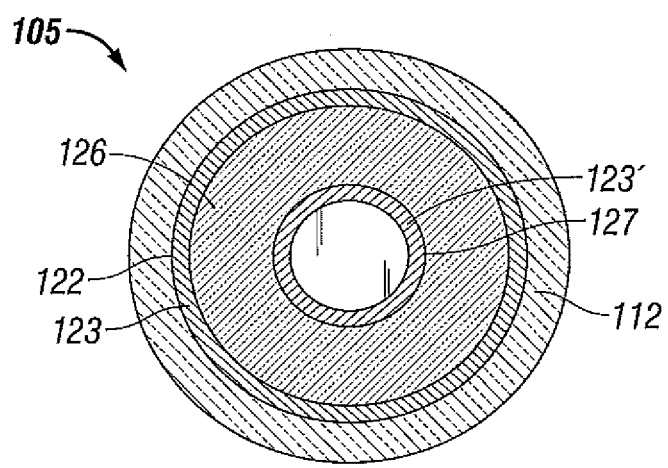
FIG. 3B is an enlarged, schematic top down view showing the electrode assembly according to FIG. 3A.

With respect to FIG. 3B, a top down view of blade assembly 105 is shown. Here, blade assembly 105 includes insulative material 126 positioned between electrode pairs 122 and 127. First and second electrodes 122, 127 are tube shaped and share a common center.

Figure 3C:
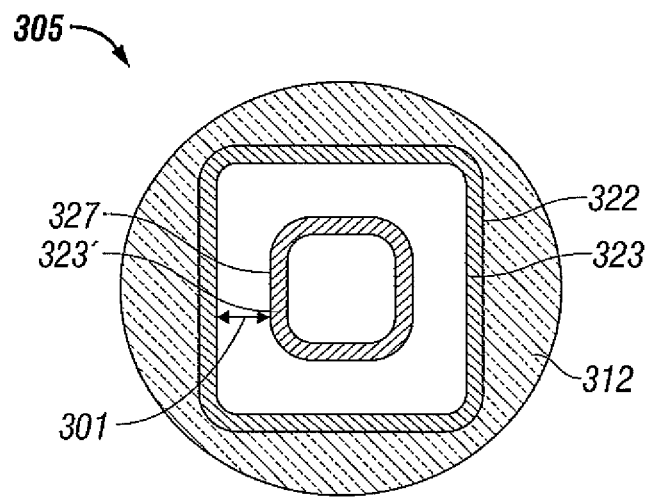
FIG. 3C is an enlarged, schematic top down view showing another blade assembly according to an embodiment of the present disclosure without an insulating layer.

While the first electrode 122 and second electrodes 127 are shown substantially tube shaped, other suitable shapes may be utilized. As best shown in FIG. 3C, non-limiting examples of other shapes include square and rectangular shaped first and second electrodes, 322 and 327, respectively, which may also share a common center. Here, first electrode assembly 305 does not include an insulative material. Rather, an insulative gap 301 is positioned between electrode pairs 322 and 327. By configuring the electrode pairs 322 and 327 and the respective air gap within close proximity to one another, the electrical power density remains high, which is important for cuffing and preventing shorts.

Figure 3D:
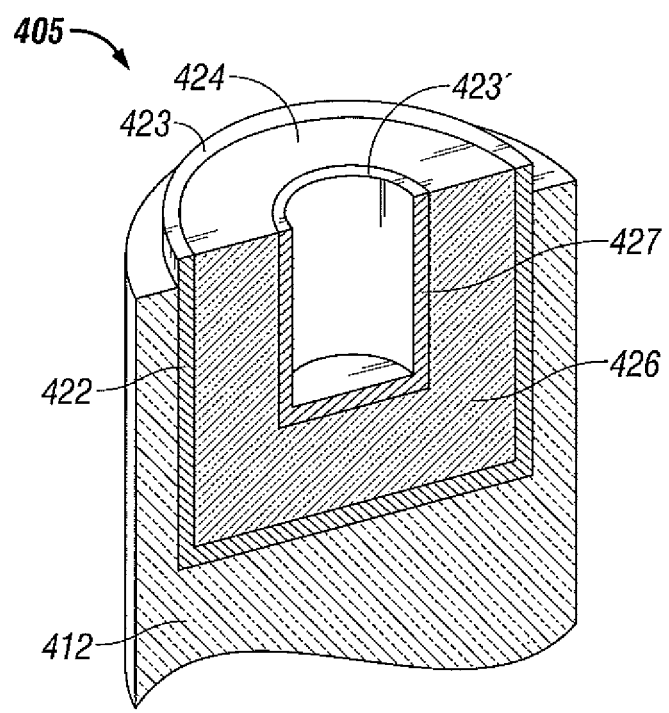
FIG. 3D is an enlarged, isometric view showing a cross-section of another blade assembly according to an embodiment of the present disclosure.

Referring now to FIG. 3D, a blade assembly 405 is shown where the first electrode 422, second electrode 427 and insulating layer 426 are substantially flush. Accordingly, distal edge 423 and 423' are substantially flush and/or share a common plane.

Figure 4A:
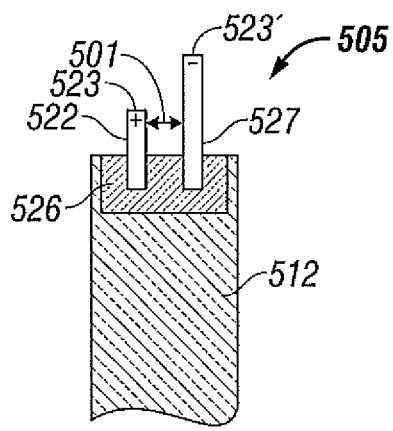
FIGS. 4A-4E are enlarged, schematic end views showing various blade assembly configurations in accordance with the an embodiment of present disclosure.

With respect to FIG. 4A, blade assembly 505 includes a first electrode 522 and second electrode 527 suitable for use as a conductive cutting element disposed substantially within or disposed on the insulator 526. The geometrical configuration and electrical arrangement of the electrode assembly 505 allows the surgeon to initially activate the opposing first electrode 522 and second electrode 527 and selectively and independently activate the distal edge 523 or 523' to cut the tissue utilizing the shown electrode assembly configuration. In such an embodiment, the first electrode 522 and second electrode 527 may be configured to electrically energize tissue such, as previously formed sealed tissue, to cut the tissue. By configuring the electrode pairs 522 and 527 and the respective air gap 501 within close proximity to one another, the electrical power density remains high, which is important for cutting and preventing shorts.

Figure 4B:
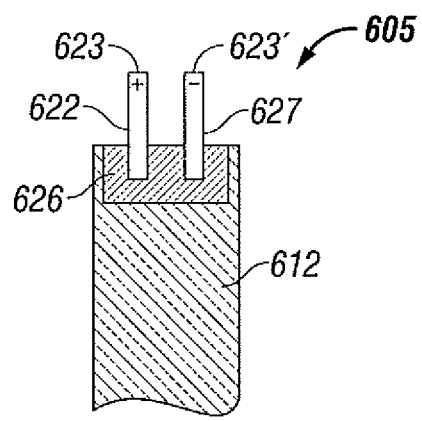

With respect to FIG. 4B, blade assembly 605 includes a first electrode 622 and second electrode 627 suitable for use as a conductive cutting element disposed substantially within or disposed on the insulator 626. In this embodiment, the first electrode 622 and second electrode 627 may be configured to electrically energize tissue such as previously formed sealed tissue, to cut the tissue. Here, the distally extending length of first electrode 622 and second electrode 627 are substantially equal. For example, first electrode 622 and second electrode 627 extend out of insulator 623 in a length of between about 0.001 inches to about 1 inch. By configuring the length of the electrode pairs 622 and 627 to be about equal, the electrical power density remains high enough to cut tissue.

Figure 4C:
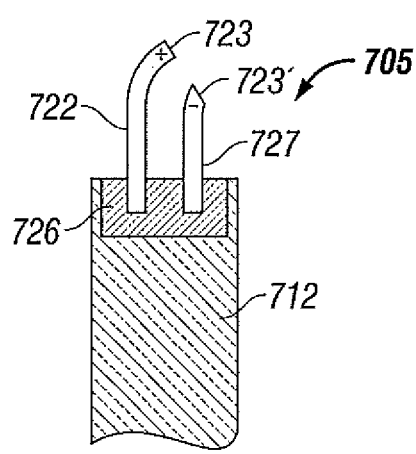

With respect to FIG. 4C, blade assembly 705 includes a first electrode 722 and second electrode 727 suitable for use as a conductive cutting element disposed substantially within or disposed on the insulator 726. The geometrical configuration and electrical arrangement of the electrode assembly 705 allow the surgeon to initially activate the opposing first electrode 722 and second electrode 727 and selectively and independently activate the distal edge 723 or 723' to cut the tissue utilizing the shown electrode assembly configuration. In such an embodiment, the first electrode 722 and second electrode 727 may be configured to electrically energize tissue, such as previously formed sealed tissue, to cut the tissue. By configuring the electrode pairs 722 and 727 in an angular and/or curved relation to one another, electrical power density remains high, while offering the surgeon an alternative configuration for applying electrical power to tissue to be cut.

Figure 4D:
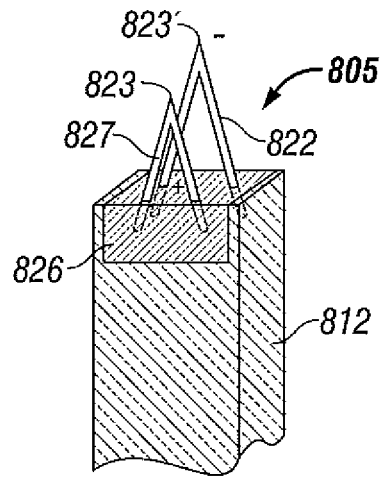

With respect to FIG. 4D, blade assembly 805 includes a first electrode 822 and second electrode 827 suitable for use as a conductive cutting element disposed substantially within or disposed on the insulator 826. First and second electrodes 822 and 827, respectively, are disposed in a fixed spaced apart relation relative to each other such that each of the electrodes function as described hereinabove without the possibility of shorts occurring between the electrodes. Alternatively, or in addition thereto, a non-conductive insulator (not explicitly shown) may be disposed between the electrodes 822, 827. The geometrical configuration and electrical arrangement of the electrode assembly 805 allow the surgeon to initially activate the opposing first electrode 822 and second electrode 827 and selectively and independently activate the distal edge 823 or 823' to cut the tissue utilizing the shown electrode assembly configuration. In such an embodiment, the first electrode 822 and second electrode 827 may be configured in a substantially triangular shape to electrically energize tissue, such as previously formed sealed tissue, to cut the tissue. The pointed shape of the first electrode 822 and second electrode 827 provide a sharp point that may be used to mechanically cut, before, during and/or after application of electrical power to first electrode 822 and second electrode 827.

Figure 4E:
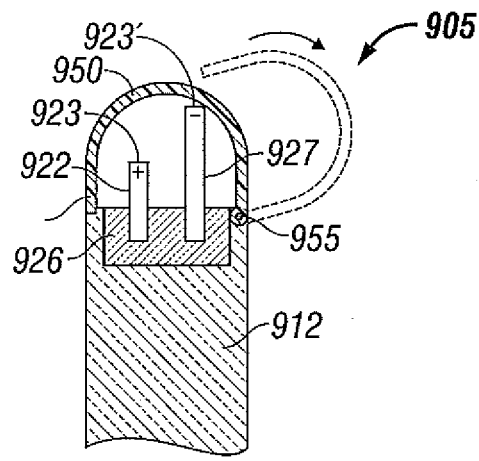

With respect to FIG. 4E, blade assembly 905 includes a first electrode 922 and second electrode 927 suitable for use as a conductive cutting element disposed substantially within or disposed on the insulator 926. A cover 950 is shown disposed over the first electrode 922 and second electrode 927. Cover 950 is shown attached to housing 12 by hinge 955; however, any suitable joint, hinge, or opening mechanism known to one of ordinary skill in the art can be used.

Various modifications may be made to the embodiments disclosed herein. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument comprising:
a blade assembly including:
a first electrode having a first pre-selected shape including a first opening defined therein, the first electrode having a first distal edge; and
a second electrode disposed in spaced relation relative to the first electrode, the second electrode having a second pre-selected shape including a second opening defined therein, the second electrode having a second distal edge, an entirety of the second distal edge being disposed radially inward of the first distal edge, a proximal-most portion of the first electrode being disposed proximally of an entirety of the second electrode, the first and second electrodes being adapted to connect to an electrosurgical energy source;
wherein the first distal edge and the second distal edge together form an electrically conductive tissue cutting surface at a distal end of the blade assembly, the tissue cutting surface being capable of conducting electrosurgical energy through tissue adjacent thereto to effectively cut tissue.

2. An electrosurgical instrument in accordance with claim 1 further comprising a first insulator configured to support each the first electrode and a second insulator configured to support the second electrode.

3. An electrosurgical instrument according to claim 2, wherein the first insulator is set back relative to the first distal edge of the first electrode and the second distal edge of the second electrode to define a recess.

4. An electrosurgical instrument in accordance with claim 1 wherein the first electrode has a first length and the second electrode has a second length, the first length being longer than the second length.

5. An electrosurgical instrument in accordance with claim 1 wherein the first electrode has a first length, and the second electrode has a second length, the first length being shorter than the second length.

6. An electrosurgical instrument in accordance with claim 1 wherein the first electrode and the second electrode are concentric.

7. An electrosurgical instrument in accordance with claim 6 wherein the first electrode and the second electrode are substantially tube-shaped.

8. An electrosurgical instrument in accordance with claim 1 further comprising a gap between the first electrode and the second electrode.

9. An electrosurgical instrument in accordance with claim 1 wherein the first electrode is an active electrode and the second electrode is a return electrode.

10. An electrosurgical instrument in accordance with claim 1 wherein the second electrode is an active electrode and the first electrode is a return electrode.

11. An electrosurgical instrument according to claim 1, wherein the first electrode and the second electrode are selectively independently activatable from one another.

12. An electrosurgical instrument according to claim 1, wherein the second distal edge of the second electrode extends proximally of the first distal edge of the first electrode.

13. An electrosurgical instrument according to claim 1, wherein the second distal edge of the second electrode is longitudinally aligned with the first distal edge of the first electrode.

14. An electrosurgical instrument according to claim 1, wherein the first distal edge of the first electrode is disposed about a longitudinal axis, and wherein a proximal-most end of the first electrode and a proximal-most end of the second electrode are each perpendicular to the longitudinal axis.

15. An electrosurgical instrument according to claim 1, wherein a proximal-most end of the first electrode and a proximal-most end of the second electrode are each parallel to each other.

16. An electrosurgical instrument according to claim 15, wherein the proximal-most end of the first electrode and the proximal-most end of the second electrode are separated by a first longitudinal gap, and wherein an insulator fills an entirety of the first longitudinal gap.

17. A bipolar electrosurgical instrument comprising:
an insulative housing,
a blade assembly having concentric first and second electrodes each having a different polarity and configured such that electrosurgical energy flows from one of the first and second electrodes to the other, the first and second electrodes disposed in a fixed spaced relation relative to one another, the blade assembly including an electrically conductive tissue cutting surface extending along a distal end of the first and second electrodes, the tissue cutting surface being adapted to connect to a source of electrosurgical energy such that the tissue cutting surface is capable of conducting electrosurgical energy through tissue contacted therewith to effect a cut, an entirety of the distal end of the second electrode being disposed radially inward of the distal end of the first electrode, a proximal-most portion of the first electrode being disposed proximally of an entirety of the second electrode; and an insulator disposed between the first and second electrodes, the first and second electrodes extending distally beyond the insulator such that the insulator defines a recessed region between the first and second electrodes at the distal end of the blade assembly.

18. An electrosurgical instrument in accordance with claim 17 wherein the first electrode has a first length extending away from the insulative housing and the second electrode has a second length extending away from the insulative housing, the first length being different than the second length.

19. An electrosurgical instrument in accordance with claim 17 wherein the first and second electrodes are substantially tube-shaped.

\* \* \* \* \*